United States Patent
Muthusamy et al.

(10) Patent No.: US 10,654,782 B2
(45) Date of Patent: May 19, 2020

(54) METHOD FOR THE PRODUCTION OF GLYCOLS FROM A CARBOHYDRATE FEED

(71) Applicant: SHELL OIL COMPANY, Houston, TX (US)

(72) Inventors: Duraisamy Muthusamy, Houston, TX (US); Viet Quoc Nguyen, Houston, TX (US); Pieter Huizenga, Amsterdam (NL)

(73) Assignee: Shell Oil Company, Houston, TX (US)

( * ) Notice: Subject to any disclaimer, the term of this patent is extended or adjusted under 35 U.S.C. 154(b) by 6 days.

(21) Appl. No.: 15/768,964

(22) PCT Filed: Oct. 18, 2016

(86) PCT No.: PCT/US2016/057446
§ 371 (c)(1),
(2) Date: Apr. 17, 2018

(87) PCT Pub. No.: WO2017/070067
PCT Pub. Date: Apr. 27, 2017

(65) Prior Publication Data
US 2019/0062243 A1    Feb. 28, 2019

Related U.S. Application Data

(60) Provisional application No. 62/243,709, filed on Oct. 20, 2015.

(51) Int. Cl.
| | | |
|---|---|---|
| *C07C 29/132* | (2006.01) | |
| *C07C 29/60* | (2006.01) | |
| *B01J 23/30* | (2006.01) | |
| *B01J 25/02* | (2006.01) | |
| *B01J 35/00* | (2006.01) | |

(52) U.S. Cl.
CPC ............ *C07C 29/60* (2013.01); *C07C 29/132* (2013.01)

(58) Field of Classification Search
CPC .............................. C07C 29/132; C07C 29/60
See application file for complete search history.

(56) References Cited

U.S. PATENT DOCUMENTS

| | | |
|---|---|---|
| 2011/0046419 A1 | 2/2011 | Zhang et al. |
| 2011/0312488 A1 | 12/2011 | Chen et al. |
| 2012/0172633 A1 | 7/2012 | Zhang et al. |
| 2015/0057469 A1 | 2/2015 | Zhang et al. |
| 2016/0304423 A1* | 10/2016 | Schreck ................... B01J 21/02 |

FOREIGN PATENT DOCUMENTS

| | | |
|---|---|---|
| WO | 2014161852 A1 | 10/2014 |
| WO | 2014173973 A1 | 10/2014 |
| WO | 2015154258 A1 | 10/2015 |
| WO | 2016114659 A1 | 7/2016 |
| WO | 2016114660 A1 | 7/2016 |
| WO | 2016114661 A1 | 7/2016 |

OTHER PUBLICATIONS

International Search Report and Written opinion received for PCT Application No. PCT/US2016/057446, dated Jan. 12, 2017, 10 pages.

* cited by examiner

*Primary Examiner* — Rosalynd A Keys

(57) ABSTRACT

Implementations of the disclosed subject matter provide methods for producing ethylene glycol from a carbohydrate feed may include contacting, in a first reactor under hydrogenation conditions, the carbohydrate feed with a bi-functional catalyst system. The bi-functional catalyst system may include a heterogeneous hydrogenation catalyst, and a soluble retro-Aldol catalyst. The carbohydrate feed may include a concentration of carbohydrate, in the total solution entering the first reactor, of 5-40 wt % in a solvent. An intermediate product stream may be obtained from the first reactor including ethylene glycol. The hydrogenation conditions may include a temperature in the range of from 180-250° C.

18 Claims, 1 Drawing Sheet

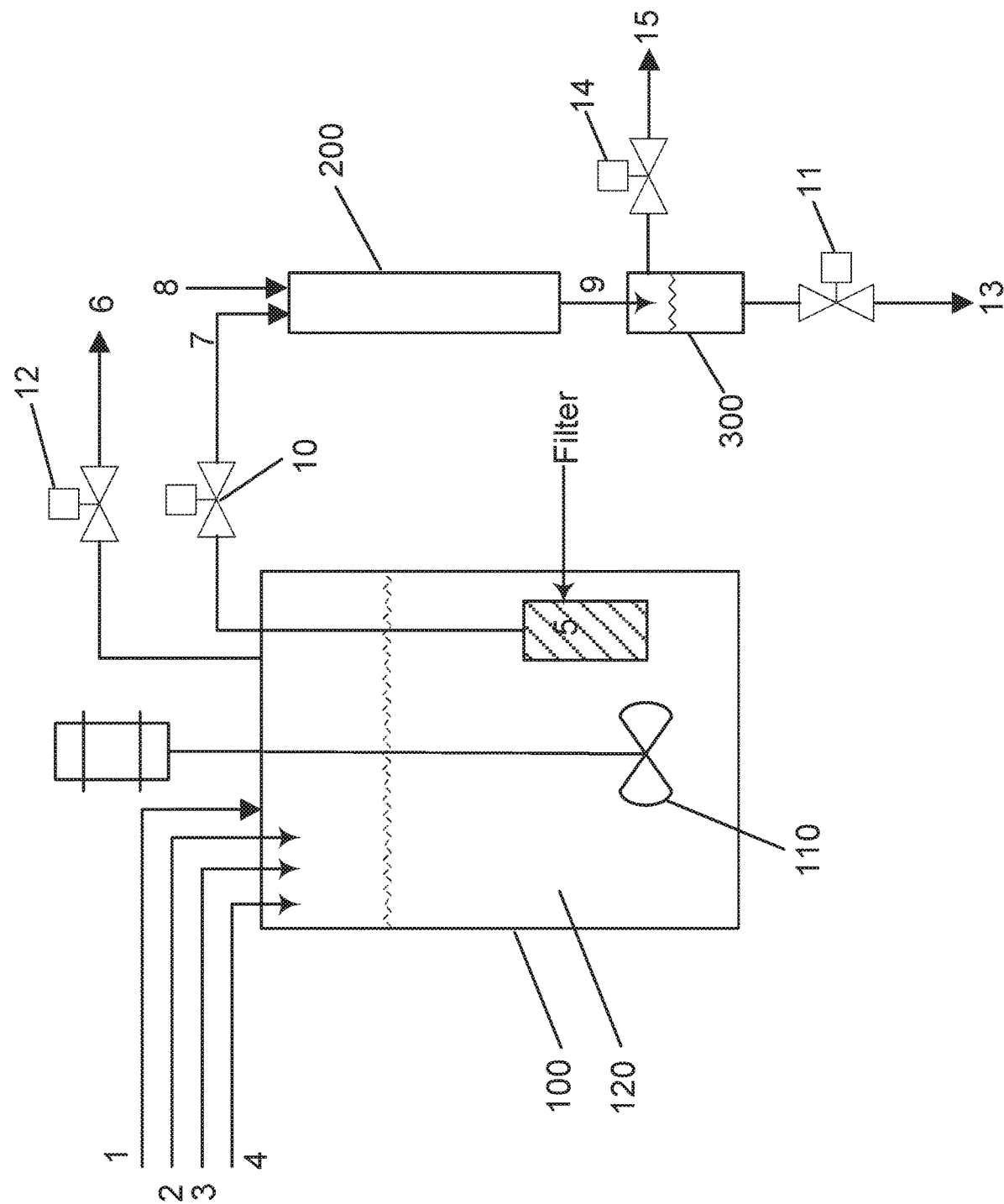

METHOD FOR THE PRODUCTION OF GLYCOLS FROM A CARBOHYDRATE FEED

CROSS-REFERENCE TO RELATED APPLICATIONS

Priority Claim

The present application is the National Stage (§ 371) of International Application No. PCT/US2016/057446, filed Oct. 18, 2016, which claims priority from U.S. Application No. 62/243,709, filed Oct. 20, 2015 incorporated herein by reference.

TECHNICAL FIELD OF THE INVENTION

The present invention relates to a process for converting a carbohydrate feed stock into glycols. More specifically the present invention relates to a process for preparing glycols, particularly ethylene glycol and propylene glycol, by converting a carbohydrate feed stock material in a reactor using a bi-functional catalyst system.

BACKGROUND

Glycols such as ethylene glycol and propylene glycol are valuable materials with a multitude of commercial applications, e.g. as heat transfer media, antifreeze, and precursors to polymers, such as PET. The market for ethylene and propylene glycols (EG and PG) is expanding worldwide, with the EG market being vastly bigger than the market for PG (i.e., 1,2-propylene glycol). Ethylene and propylene glycols are typically made on an industrial scale by hydrolysis of the corresponding alkylene oxides, which are the oxidation products of ethylene and propylene, produced from fossil fuels/petrochemical feed stocks involving multiple processing steps. Use of bio-based feed stocks for the production of energy and chemicals has become increasingly desirable in the industry since this approach to use feeds from renewable sources provides a pathway for sustainable development.

In recent years, increased efforts have focused on producing chemicals, including glycols, from renewable feedstocks, such as carbohydrate-containing feedstock. Carbohydrates are plentiful and renewable bio-mass feeds having the structural features resembling that of ethylene glycol; each carbon has one attached hydroxyl group or contains an oxygen function that can be readily converted into a hydroxyl. As such, EG and PG can be produced if the C—C bonds are selectively cleaved into $C_2$ and $C_3$ units.

As with many chemical processes, the reaction product stream in these processes comprises a number of desired materials as well as diluents, by-products and other undesirable materials. In order to provide a high value process, the desirable product or products must be obtainable from the reaction product stream in high purity with a high percentage recovery of each product and with as low as possible use of energy, chemical components and complex equipment.

Therefore, it would be advantageous to provide an improved method suitable for the production of glycols from carbohydrate feeds in order to make the overall glycol production process more economical than processes disclosed previously in the industry.

BRIEF SUMMARY

According to an embodiment of the disclosed subject matter, a method for producing ethylene glycol from a carbohydrate feed may include contacting, in a first reactor under hydrogenation conditions, the carbohydrate feed with a bi-functional catalyst system. The bi-functional catalyst system may include a heterogeneous hydrogenation catalyst, and a soluble retro-Aldol catalyst. The carbohydrate feed may include a concentration of carbohydrate, in the total solution entering the first reactor, of 5-40 wt % in a solvent. An intermediate product stream may be obtained from the first reactor including ethylene glycol. The hydrogenation conditions may include a temperature in the range of from 180-250° C.

Implementations of the disclosed subject matter provide an improved method for producing ethylene glycol from a carbohydrate feed. The disclosed subject matter allows the desirable products of EG and PG to be obtained from the reaction product stream in high purity with a high percentage recovery of each product and with relatively low use of energy, chemical components and complex equipment as compared to prior processes. This method results in a production of glycols from carbohydrate feeds that makes the overall glycol production process more economical than processes disclosed previously in the industry. Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

FIG. 1 shows an example process scheme according to an implementation of the disclosed subject matter.

DETAILED DESCRIPTION

Carbohydrates are readily available and renewable bio-mass feeds, and they have the structural features resembling that of ethylene glycol; each carbon has one attached hydroxyl group or contains an oxygen function that can be readily converted into a hydroxyl. Ethylene glycol (EG) and propylene glycol (PG) can be produced by selectively cleaving the C—C bonds into $C_2$ and $C_3$ units. As such, the presently disclosed subject matter provides a process for the conversion of carbohydrate feed stock materials and hydrogen gas into glycols, particularly with ethylene glycol as the main product and propylene glycol as a smaller co-product.

The process variables have major impacts on the conversion and selectivity of the reaction. For example, the particular catalyst(s) used and process conditions can provide for a successful reaction selectivity outcome under a set of practical reaction conditions. Examples of process variables include feed stock (e.g., sucrose, glucose, sorbitol, $C_5$ versus $C_6$ sugars, starch, and the like); one or more catalysts (e.g., having retro-Aldol and hydrogenation functions); temperature, $H_2$ partial pressure, $H_2$/feed ratio, residence time, reaction medium (e.g., a solvent such as water), pH in the reaction medium, and feed/solvent ratio. According to the presently disclosed subject matter, these process variables are identified as being important taking into consideration the chemistry of the reaction discussed below.

The sugars to glycols hydrogenolysis reaction, which is carried out using a metal catalyst and in the presence of hydrogen, is a complex reaction known to produce hundreds of products. Since ethylene and propylene glycols are the desired products, the other products must be minimized by selecting the appropriate catalyst and conditions; additionally an EG/PG wt % ratio of at least 1:1 and preferably 7:1 or more is desirable. In general, sugars tend to cleave into $C_3$ fragments more easily than the desired $C_2$ fragment, resulting in the formation of propylene glycol as the single most predominant molecule. While the selection of the most appropriate catalyst, not only from the selectivity point of view but also from the point of view of catalyst longevity, is an important task, other aspects of the reaction must also be considered. The catalyst generally only controls the chemistry taking place on its surface; for example, the cleavage of the sugar molecules into smaller fragments taking place by discrete retro-Aldol reactions followed by hydrogenation of the intermediates into products is the desired pathway. However, quite a number of other reactions take place in solution and these side reactions must also be considered. A number of ions such as OH—, OAc—, etc. could be present in the solution under basic pH conditions or H+ ions could be present under acidic pH conditions. While these ions could also catalyze the retro-Aldol reaction, these ions are generally known to catalyze a variety of dehydration side-reactions causing the sugar molecules to degrade into wasteful products. These undesirable side reactions could become dominant particularly under high temperature conditions. A proper choice of catalysts and process conditions is therefore essential in order to realize the objectives of high glycol yields and long catalyst life. Multiple equations can be used to explain the various steps of the chemistry of the conversion of sugars to EG and PG, as shown below.

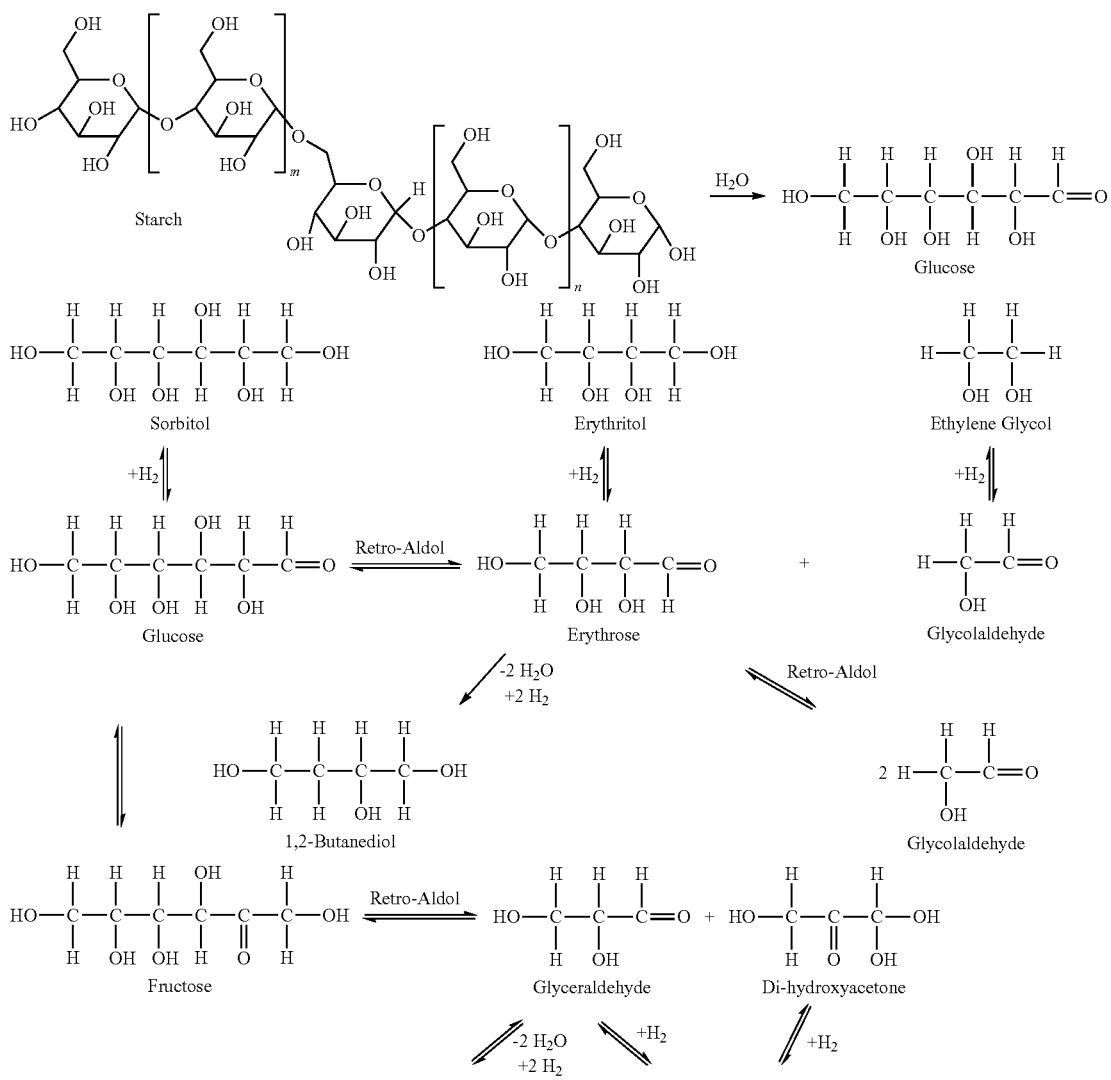

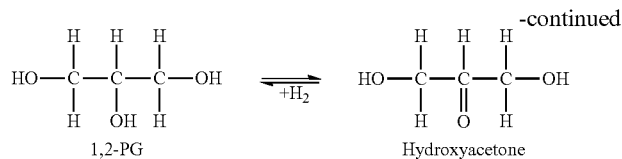
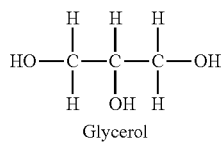

As shown above, the chemistry of sugars in the hydrogenolysis reaction is a notoriously complex set of functional group chemistries; the products from any reaction could be reactants for all other reactions, including those taking place on the surface of the solid catalyst. The product distribution (EG, PG, partially converted sugars, etc.) at the end of reaction will be a function of the relative rates of these reactions under the chosen experimental conditions. Thus, according to the presently disclosed subject matter, important process variables have been determined for the disclosed method for producing ethylene glycol from a carbohydrate feed.

The presently disclosed method for producing ethylene glycol from a carbohydrate feed has numerous advantages over the prior art. The disclosed method provides for various process conditions that, when combined, achieve superior results in terms of product yield, catalyst stability, and extended run time (e.g., suitable for commercialization). The presently disclosed method allows for the use of a carbohydrate feed with a high carbohydrate concentration and may also include running the reaction under pH controlled conditions. As a result, the presently disclosed method has the advantages of achieving high total glycol yield (i.e., EG, PG, 1,2 butanediol "hereinafter 1,2BDO or 12BDO"), high EG:PG ratio, high EG:1,2BDO ratio, and having a stable catalyst system for at least 24 hours, at least 50 hours, and at least 100 hours.

According to an implementation of the disclosed subject matter, a method for producing ethylene glycol from a carbohydrate feed may include contacting, in a reactor under hydrogenation conditions, the carbohydrate feed with a bi-functional catalyst system. The carbohydrate feed for the process may include one or more of glucose, sucrose, xylose, sugar cane molasses, starch (e.g., hydrolyzed starch, corn syrup, and the like), and cellulose (e.g., hydrolyzed cellulose, and the like). In an embodiment, the carbohydrate feed may include a concentration of carbohydrate, in the total solution entering the reactor of 5-40 wt % in a solvent, at least 5 wt % in a solvent, and at least 10 wt % in a solvent.

The solvent may be water, a $C_1$ to $C_6$ alcohol, a $C_1$ to $C_6$ polyol, or mixtures thereof. Further solvent may also be added to the reactor in a separate feed stream or may be added to the carbohydrate feed before it enters the reactor. Examples of $C_1$ to $C_6$ polyols include 1,2-hexanediol, glycerol, etc. As an example, the solvent may be a mixture including $H_2O$ and at least one of alcohols, ethers, and ether-alcohols, and mixtures thereof. In an embodiment, the solvent may be $H_2O$.

Suitable reactor vessels to be used in the process of the preparation of ethylene glycol from a carbohydrate feed include continuous stirred tank reactors (CSTR), plug-flow reactors, slurry reactors, ebbulated bed reactors, jet flow reactors, mechanically agitated reactors, back-mixed reactors, bubble columns, such as slurry bubble columns and external recycle loop reactors. The use of these reactor vessels allows dilution of the reaction mixture to an extent that provides high degrees of selectivity to the desired glycol product (mainly ethylene and propylene glycols). There may be one or more of such reactor vessels, arranged in series. In one embodiment, preferably there are two reactor vessels arranged in series, the first one of which is a CSTR, the output of which is supplied into a plug-flow reactor.

The disclosed method for producing ethylene glycol from a carbohydrate feed may be performed under particular hydrogenation conditions in order to maximize the desired yield of EG. For example, the hydrogenation conditions may include temperature, pressure, flow rate, and any other process variable that may be controlled. In an embodiment, the hydrogenation conditions may include a temperature in the range of from 180-250° C. and from 210-250° C. The hydrogenation conditions may also include a pressure in the range of from 500 to 2000 psig.

In an embodiment, the presently disclosed method may also include contacting the carbohydrate feed with hydrogen. For example, the disclosed method may take place in the presence of hydrogen. Hydrogen may be supplied into the reactor vessel under pressure in a manner common in the art. Hydrogen is supplied into the reactor vessels under pressure. In an example, the method of the present reaction takes place in the absence of air or oxygen. In order to achieve this, it is preferable that the atmosphere in the reactor vessel be evacuated and replaced with hydrogen repeatedly, after loading of any initial reactor vessel contents, before the reaction starts.

According to an embodiment, the bi-functional catalyst system may include a heterogeneous hydrogenation catalyst, and a soluble retro-Aldol catalyst. The heterogeneous hydrogenation catalyst may comprise one or more materials selected from transition metals from groups 8, 9, 10, 11 or compounds thereof, with catalytic hydrogenation capabilities. The heterogeneous hydrogenation catalyst may comprise one or more of iron, cobalt, nickel, ruthenium, rhodium, palladium, iridium and platinum. This heterogeneous hydrogenation catalyst may be present in the elemental form or as a compound. It may also be suitable that this heterogeneous hydrogenation catalyst is present in chemical combination with one or more other ingredients in the catalyst system. In an embodiment, the heterogeneous hydrogenation catalyst may be a Raney-type catalyst. According to an embodiment, the heterogeneous hydrogenation catalyst may comprise at least one of Raney-Ni, Raney-Co, Raney-Cu, Raney-Ru, Cu, Co, Ru, and, nano-particle metal. According to an implementation, the heterogeneous hydrogenation catalyst may be a nano-particle metal comprising any metal selected from Groups 8, 9, 10, or 11. In some cases, the heterogeneous hydrogenation catalyst may be further promoted with one or more metals such as Fe, Cr, Mn, Mo, W, Re, Rh, Pd, Ag, Au, Pt, Ir, and La. In an embodiment, the heterogeneous hydrogenation catalyst may be provided in sulfided form.

The soluble retro-Aldol catalyst may comprise one or more compound, complex or elemental material comprising tungsten, molybdenum, vanadium, niobium, chromium, titanium or zirconium. In particular, the soluble retro-Aldol catalyst may comprise one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. According to an embodiment, examples of the soluble retro-Aldol catalyst may include at least one of: silver tungstate, sodium metatungstate, ammonium meta-tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silicotungstic acid, alkali- and alkaline-earth metal niobates.

According to an embodiment, at least one of the heterogeneous hydrogenation catalyst and soluble retro-Aldol catalyst of the bi-functional catalyst system is supported on a solid support. In an embodiment, any other active catalyst component may be present in either heterogeneous or homogeneous form. In this case, any other active catalyst component may also be supported on a solid support. In one embodiment, the heterogeneous hydrogenation catalyst is supported on one solid support and the soluble retro-Aldol catalyst is supported on a second solid support which may comprise the same or different material. As a specific example, the heterogeneous hydrogenation catalyst may be a hydrogenation catalyst supported on a hydrothermally stable support. In another embodiment, both the heterogeneous hydrogenation catalyst and soluble retro-Aldol catalyst are supported on one solid hydrothermally stable support.

The solid support may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In an embodiment, the disclosed method may also include running the reaction under pH controlled conditions. In particular, the pH of the reaction may be in the range of from 2-7. The pH may be controlled using at least one pH controlling agent such as alkali- and alkaline-earth metal salts of carbonic acid or carboxylic acids or combinations thereof, alkali- and alkaline-earth metal salts of phosphoric acid, zinc carbonate, and zinc salts of carboxylic acids.

According to the presently disclosed subject matter, an intermediate product stream may be obtained from the reactor including ethylene glycol. The intermediate product stream may include at least 5 wt % concentration of glycols. In addition, the intermediate product stream may include a yield of at least 60 wt % glycols, and at least 70 wt % glycols. In an embodiment, the intermediate product stream may include a yield of at least 60 wt % EG, and at least 65 wt % EG. An advantage of the presently disclosed method is the ability to maximize the yield of EG relative to the yield of PG. For example, the intermediate product stream may include an EG/PG wt % yield ratio of at least 1:1, a EG/PG wt % yield ratio of at least 7:1, and a EG/PG wt % yield ratio of at least 10:1. In addition, the presently disclosed method allows for minimizing undesired products of the subject reaction. Accordingly, the intermediate product stream may include a yield of no more than 10 wt % sorbitol. Further, the intermediate product stream may include a yield of less than 3 wt % 1,2-butanediol. Additionally, the product stream may include a minimum EG/1,2BDO wt % yield ratio of 20:1, thereby maximizing the EG yield relative to other less desired products.

FIG. 1 shows an example process scheme according to an implementation of the disclosed subject matter. As shown in FIG. 1, reactor 100 may include an agitator 110 for mixing the solution 120. In one example, the heterogeneous hydrogenation catalyst with water (e.g., a slurry of the catalyst and water) may be pre-loaded in the reactor 100. The heterogeneous hydrogenation catalyst is activated by reduction with hydrogen supplied through feed line 1. Next, the temperature may be increased to the desired reaction temperature. Feed line 2 may be a carbohydrate feed (e.g., a glucose solution) fed to the reactor 100. Feed line 3 may be used for feeding the soluble retro-Aldol catalyst into reactor 100. In an example, the reactor 100 may be pre-loaded with the heterogeneous hydrogenation catalyst and the soluble retro-Aldol catalyst may be continuously added to the reactor 100. In one embodiment, the soluble retro-Aldol catalyst may be continuously added to the reactor 100 via the carbohydrate feed 2. Feed line 4 may be used to feed a pH controlling additive for controlling the pH in the reactor 100. In some cases, the pH within the reactor 100 may be controlled without the use of a pH controlling additive. Two or more of the liquid feeds may be combined into one or more feed lines 2-4. The pressure in reactor 100 may be controlled by pressure control valve 12 and excess hydrogen may be vented from reactor 100 via an off-gas line 6. Off-gas line 6 may also contain light components of the reaction, for example, methane, carbon monoxide, carbon dioxide, etc. A level controlling device (not shown) may measure the volume within reactor 100 in order to maintain a constant volume. The liquid intermediate product stream 7 may be removed from reactor 100 via filter 5. Filter 5 may be used to separate the solid components of the bi-functional catalyst system from the liquid intermediate product stream 7, thereby maintaining the solid components in the reactor 100. A level control valve 10 may be used to control the flow of intermediate product stream 7 in order to maintain the desired constant volume of reactor 100. Intermediate product stream 7 may be fed to reactor 200. Reactor 200 may be loaded with a fixed bed hydrogenation catalyst. This step may be performed in order to perform a polishing hydrogenation of intermediate product stream 7. Feed line 8 may be used to feed hydrogen to the reactor 200. A gas/liquid mixture from reactor 200 may be removed from reactor 200 via product stream 9. Product stream 9 may be in-line cooled and fed to gas/liquid separator 300. A pressure control valve 14 may be used to control the pressure inside reactor 200 and gas/liquid separator 300. A level control valve 11 may be used to control the level in gas/liquid separator 300. Product stream 13 may remove the final liquid product from the gas/liquid separator 300. Excess gas may be vented from gas/liquid separator 300 via gas stream 15.

According to an implementation of the disclosed subject matter, the intermediate product stream may be fed to a second reactor. In the second reactor, the intermediate product stream from the first reactor may be contacted with hydrogen in the presence of a heterogeneous hydrogenation catalyst. As a result, a final product stream may be obtained comprising ethylene glycol that is substantially free of compounds containing carbonyl functional groups. As shown in FIG. 1 and mentioned above, intermediate product stream 7 may be fed to reactor 200. Reactor 200 may be loaded with a fixed bed hydrogenation catalyst. This step may be performed in order to perform a polishing hydrogenation of intermediate product stream 7. Feed line 8 may be used to feed hydrogen to the reactor 200. Effluent from reactor 200 may be removed from reactor 200 via product stream 9. If a catalyst system is present in the second reactor, the catalyst system used in each of the first and second reactors may be the same or different. A further advantage of the invention is that different catalysts, tailored to the feed being supplied to each reactor, may be used in each reactor.

In the disclosed method for the preparation of ethylene glycol from a carbohydrate-containing feed, the residence time in the reactor vessel of the reaction mixture may be at least 1 minute, at least 2 minutes, and at least 5 minutes. Suitably the residence time in the reactor vessel is no more than 5 hours, no more than 2 hours, and no more than 1 hour. According to an implementation, the average residence time in the reactor is no more than 2 hours.

A feature of the presently disclosed subject matter is the ability to run the reaction for a time period of at least 100 hours. In particular, the disclosed process may include running the reaction for a time period of at least 100 hours with a stable catalyst system.

As shown in the Examples section provided below, the presently disclosed method for producing ethylene glycol from a carbohydrate feed has numerous advantages over the prior art. The disclosed method provides for various process conditions that, when combined, achieve superior results in terms of product yield, catalyst stability, and extended run time (e.g., suitable for commercialization). The presently disclosed method allows for the use of a carbohydrate feed with a high carbohydrate concentration and by running the reaction under pH controlled conditions, superior results and advantages over the prior art are achieved. As a result, the presently disclosed method has the advantages of achieving high total glycol yield (i.e., EG, PG, 1,2BDO), high EG:PG ratio, high EG:1,2BDO ratio, and having a stable catalyst system for at least 24 hours, at least 50 hours, and at least 100 hours.

EXAMPLES

Experimental Apparatus

The apparatus used to perform the experiments shown in Examples 1 to 3 is schematically represented in FIG. 1. A one-liter Hastelloy-C autoclave, Reactor 100, was equipped with automatic controls for the control of reactor temperature, back-pressure, liquid level, and stirrer speed. The feed line-1 was equipped with a gas flow meter and was used to provide a continuous flow of hydrogen gas into the reactor. Each of the liquid feed lines 2 to 4, was equipped with a pump and a mass flow meter. These lines were used to continuously feed the solutions containing the glucose feed, the sodium meta-tungstate retro-Aldol catalyst, and the NaHCO$_3$ pH control agent. Filter element 5 was used to retain the heterogeneous hydrogenation catalyst inside the reactor while allowing the flow of the liquid product, which was controlled by valve-10, via line 7. The excess gas pressure present in the reactor was vented via line 6 by the use of the back-pressure control valve-12.

Reactor 200 was a 32"×1" tubular reactor with a 15" tall catalyst section in the middle. This reactor was equipped with heater temperature controls and inside thermocouples for measuring the temperature of the catalyst bed. The gas feed line-8 was equipped with a flowmeter and was used to continuously feed hydrogen to reactor 200. Line-9 was an in-line product cooler with the ability to cool down the product mixture to or below room temperature. The gas-liquid product effluent passing through line-9 was set up to flow into a gas-liquid separator 300. Valve-14 was used to control the back-pressure of Reactor 200. Valve-11 was used to control the level in the gas-liquid separator. Samples of the product stream were taken via line-13 for analysis. Experimental results are reported in the following examples.

Materials:

Glucose, Raney-nickel (WR Grace Raney-nickel 2800), sodium meta-tungstate (NaMT), sodium bicarbonate (NaHCO$_3$), ethylene glycol (EG), 1,2-propylene glycol (PG), 1,2-butanediol (12BDO), glycerol were purchased from Sigma-Aldrich chemical company.

Analytical Methods:

In the Examples provided below, pH measurements were made using Thermo Scientific's Orion Star A211 bench top pH meter and the meter was calibrated with standard buffer solutions in the 4-10 pH range.

HPLC analysis of the liquid samples was performed using the following method and conditions: Liquid Chromatography System—Shimadzu; Controller—SCL-10Avp; Pump—LC-20AD; Degasser—DGU-20A 5r; Autosampler—SIL-10AF; Column Oven—CTO-20AC; UV detector—SPD-20AV; RI detector—RID-10A.

HPLC instrument conditions: Column: Bio-Rad Aminex HPX-87H (300 mm×7.8 mm); Flow Rate: 0.6 ml/minute; Column Oven: 30 C; Injection Volume: 10 µl; UV Detector: @320 NM; RI Detector: mode—A; range—100; Run Time: 66 minute; Mobile Phase: 5 mM Sulfuric Acid in water.

Standard solutions containing glucose, sorbitol, ethylene glycol (EG), 1,2-propylene glycol (PG), 1,2-butanediol (12BDO), glycerol, erythritol, threitol, xylitol, etc. were prepared using water as the solvent at various concentrations. These solutions were analyzed to create the HPLC calibration curves. Samples were analyzed, with or without further dilution, and the calibration factors were applied to calculate the concentrations of the various products present in the experimental samples.

Example 1 Production of Glycols from Glucose Using Raney-Ni, Sodium Meta-Tungstate, and NaHCO$_3$ In this example, 21.27 grams of a sample of WR Grace Raney-nickel 2800 was added to the autoclave (Reactor 100) as slurry in 500 ml of water. The autoclave level control was set up to maintain 500 ml of liquid holdup volume in the reactor. A continuous flow of hydrogen was provided and the reactor pressure was controlled in the range of 1000 psig. The catalyst was washed with deionized water at a rate of 5 ml per minute until the pH of the reactor effluent reached near neutrality. The catalyst was then activated by ramping up the temperature to 100° C. and holding at temperature overnight.

The fixed-bed catalyst reactor 200 was loaded with 92.5 grams of a 1% Ru-on-ZrO$_2$ catalyst diluted with a 1:1 volume silicon carbide, 90 milliliters each, in the 15" tall catalyst section at the beginning of a previous run. This catalyst is typically activated by reduction with hydrogen before putting it to use. The used catalyst from the previous run was freshly activated by a standard decoking and reactivation procedure just before starting the run that contains the current example.

Two separate feed solutions were prepared using deionized water as solvent, one solution containing 10.0% wt concentration of glucose and 0.50% wt concentration of sodium meta-tungstate (NaMT) retro-Aldol catalyst and the other containing 1.0% wt concentration of NaHCO$_3$ as the pH control agent. As part of an ongoing continuous run, these feed solutions were pumped into Reactor 100 starting at the run time of 331 hours and continued for at least a 100 hour period. The following experimental conditions for Reactor 100 were used during this period: combined liquid feed rate of approximately 390 grams per hour, reaction temperature of 230° C., pressure of 1500 psig, hydrogen flow rate of 25 standard liters per hour, and stirrer RPM of 1500. The following conditions for Reactor 200 were used: reactor temperature of 150° C., pressure of 1250 psig and hydrogen flow rate of 15 standard liters per hour.

Samples of product stream 13 were analyzed by pH probe and HPLC to determine pH and the concentrations of the various products. The experimental results are given in Table 1 below.

%, and in particular, on average 5.47 wt %. The total glycols yield was on average 69.8 wt %, with some samples showing greater than 70 wt %. Another desired result is a yield of less than 10 wt % sorbitol, and as shown, an average sorbitol yield of 8.5 wt % was achieved. Another feature of the presently disclosed subject matter is the ability to maximize the production of EG relative to PG. As shown, the disclosed process achieved a yield of at least 60 wt % EG, specifically, an average of 62.4 wt % EG. Further, an EG/PG wt % yield ratio of at least 7:1 is desired, and as shown, on average 11.5:1 EG/PG wt % yield ratio is achieved. The amount of 1,2-butanediol is minimized with a yield of less than 3 wt % 1,2-butanediol, and specifically, on average less than 2 wt % 1,2-butanediol as shown.

Example 2 Production of Glycols from Glucose Using Raney-Ni and Sodium Meta-Tungstate In this example, 30.61 grams of a sample of WR Grace Raney-nickel 2800 was added to the autoclave (Reactor 100) as slurry in 500 ml of water. The autoclave level control was set up to maintain 500 ml of liquid holdup volume in the reactor. A continuous flow of hydrogen was provided and the reactor pressure was controlled in the range of 1000 psig. The catalyst was washed with deionized water at a rate of 5 ml per minute until the pH of the reactor effluent reached near neutrality. The catalyst was then activated by ramping up the temperature to 100° C. and holding at temperature overnight.

A single feed solution using deionized water as solvent was prepared and it contained 10.0% wt concentration of

TABLE 1

| Run Time [Hour] | Sample | *Conc to Rxn Mixture, % Wt | | | Conc in Product Total Glycols, % Wt | pH | % Wt Yields | | | | | Total Glycols | Wt Ratio EG/PG |
|---|---|---|---|---|---|---|---|---|---|---|---|---|---|
| | | Glucose | NaHCO3 | NaMT | | | Glucose | Sorbitol | EG | PG | 12BDO | | |
| 335.2 | 1A | 8.36 | 0.164 | 0.418 | 5.93 | 4.0 | 0.2 | 10.8 | 61.7 | 6.9 | 2.4 | 71.0 | 9.0 |
| 338.5 | 1B | 8.36 | 0.164 | 0.418 | 5.81 | 4.0 | 0.2 | 8.8 | 62.2 | 5.4 | 1.9 | 69.6 | 11.5 |
| 353.9 | 1C | 8.36 | 0.164 | 0.418 | 5.81 | 3.4 | 0.2 | 8.0 | 62.5 | 4.9 | 2.1 | 69.5 | 12.8 |
| 358.2 | 1D | 7.67 | 0.233 | 0.384 | 5.31 | 4.0 | 0.2 | 8.7 | 62.0 | 5.3 | 1.9 | 69.1 | 11.8 |
| 362.2 | 1E | 7.67 | 0.233 | 0.384 | 5.17 | 4.0 | 0.2 | 9.1 | 60.2 | 5.3 | 1.9 | 67.3 | 11.3 |
| 377.9 | 1F | 7.67 | 0.233 | 0.384 | 5.25 | 4.1 | 0.2 | 9.4 | 60.9 | 5.5 | 1.9 | 68.4 | 11.0 |
| 382.7 | 1G | 7.67 | 0.233 | 0.384 | 5.60 | 3.6 | 0.2 | 9.1 | 65.7 | 5.3 | 2.0 | 73.0 | 12.4 |
| 386.1 | 1H | 7.67 | 0.233 | 0.384 | 5.62 | 4.0 | 0.2 | 8.3 | 66.1 | 5.1 | 2.0 | 73.3 | 12.9 |
| 401.5 | 1I | 7.67 | 0.233 | 0.384 | 5.34 | 4.1 | 0.2 | 7.8 | 62.2 | 5.4 | 2.0 | 69.5 | 11.6 |
| 404.7 | 1J | 7.67 | 0.233 | 0.384 | 5.36 | 4.0 | 0.2 | 7.6 | 62.4 | 5.4 | 2.0 | 69.8 | 11.6 |
| 410.2 | 1K | 7.67 | 0.233 | 0.384 | 5.25 | 4.1 | 0.2 | 8.0 | 60.9 | 5.6 | 2.0 | 68.4 | 10.9 |
| 433.4 | 1L | 7.67 | 0.233 | 0.384 | 5.29 | 3.9 | 0.2 | 7.5 | 61.6 | 5.3 | 2.0 | 68.9 | 11.6 |
| 437.5 | 1M | 7.67 | 0.233 | 0.384 | 5.37 | 4.0 | 0.2 | 7.4 | 62.5 | 5.4 | 2.1 | 70.0 | 11.6 |
| Average = | | 7.83 | 0.217 | 0.392 | 5.47 | 3.9 | 0.2 | 8.5 | 62.4 | 5.4 | 2.0 | 69.8 | 11.5 |

As shown in Table 1 above, a process according to the presently disclosed subject matter included contacting a carbohydrate feed with a bi-functional catalyst system (i.e., Raney-Ni, and sodium meta-tungstate. This example process was run for greater than 100 hours. The carbohydrate feed included a concentration of carbohydrate (i.e., glucose) of on average 7.83 wt %. The pH control agent NaHCO$_3$ was used to control the pH of the reaction to be in the range of from 2-7, and in particular, on average a pH of 3.9. According to the presently disclosed subject matter, various advantages regarding product yields are achieved. As shown, the concentration of glycols in the product stream is at least 5 wt glucose and 0.30% wt concentration of sodium meta-tungstate (NaMT) retro-Aldol catalyst.

This run was started by placing Reactor 200 in bypass mode. The following experimental conditions for Reactor 100 were used for this run: liquid feed rate of 294 grams per hour, reaction temperature of 230° C., pressure of 1500 psig, hydrogen flow rate of 25 standard liters per hour, and stirrer RPM of 1500.

Samples of product stream 13 were analyzed by pH probe and HPLC to determine pH and the concentrations of the various products. The experimental results are given in Table 2.

TABLE 2

| Run Time [Hour] | Sample | *Conc to Rxn Mixture, % Wt | | Conc in Product Total Glycols, % Wt | pH | % Wt Yields | | | | | Total Glycols | Wt Ratio EG/PG |
|---|---|---|---|---|---|---|---|---|---|---|---|---|
| | | Glucose | NaMT | | | Glucose | Sorb | EG | PG | 12BDO | | |
| 7.9 | 2A | 10.00 | 0.300 | 7.49 | 3.5 | 0.2 | 7.2 | 71.6 | 2.0 | 1.3 | 74.9 | 35.5 |
| 23.4 | 2B | 10.00 | 0.300 | 7.52 | 3.7 | 0.2 | 9.1 | 71.5 | 2.4 | 1.3 | 75.2 | 29.9 |
| 27.9 | 2C | 10.00 | 0.300 | 7.36 | 3.8 | 0.2 | 9.9 | 70.0 | 2.3 | 1.3 | 73.6 | 30.0 |
| 31.8 | 2D | 10.00 | 0.300 | 7.33 | 3.8 | 0.2 | 9.9 | 69.9 | 2.2 | 1.3 | 73.3 | 32.1 |
| 47.3 | 2E | 10.00 | 0.300 | 7.30 | 3.9 | 0.2 | 9.9 | 69.4 | 2.3 | 1.3 | 73.0 | 30.2 |
| 50.3 | 2F | 10.00 | 0.300 | 7.32 | 3.9 | 0.2 | 10.1 | 69.3 | 2.5 | 1.4 | 73.2 | 28.3 |
| 54.2 | 2G | 10.00 | 0.300 | 7.23 | 3.9 | 0.2 | 10.5 | 68.4 | 2.5 | 1.4 | 72.3 | 27.5 |
| 71.7 | 2H | 10.00 | 0.300 | 7.03 | 3.8 | 0.2 | 11.4 | 66.0 | 2.8 | 1.5 | 70.3 | 23.8 |
| Average = | | 10.00 | 0.300 | 7.32 | 3.8 | 0.2 | 9.8 | 69.5 | 2.4 | 1.3 | 73.2 | 29.7 |

As shown in Table 2 above, a process according to the presently disclosed subject matter included contacting a carbohydrate feed with a bi-functional catalyst system (i.e., Raney-Ni, and sodium meta-tungstate. This example process was run for greater than 70 hours. The carbohydrate feed included a concentration of carbohydrate (i.e., glucose) of on average 10 wt %. The pH of the reaction was controlled to be in the range of from 2-7, and in particular, on average a pH of 3.8. According to the presently disclosed subject matter, various advantages regarding product yields are achieved. As shown, the concentration of glycols in the product stream is at least 5 wt %, and in particular, on average 7.32 wt %. The total glycols yield was on average 73.2 wt %, with some samples showing greater than 75 wt %. Another desired result is a yield of less than 10 wt % sorbitol, and as shown, an average sorbitol yield of 9.8 wt % was achieved. Another feature of the presently disclosed subject matter is the ability to maximize the production of EG relative to PG. As shown, the disclosed process achieved a yield of at least 60 wt % EG, specifically, an average of 69.5 wt % EG. Further, an EG/PG wt % yield ratio of at least 7:1 is desired, and as shown, on average 29.7:1 EG/PG wt % yield ratio is achieved. The amount of 1,2-butanediol is minimized with a yield of less than 3 wt % 1,2-butanediol, and specifically, on average less than 1.3 wt % 1,2-butanediol as shown.

Comparative Example 3 Production of Glycols from Glucose Using Raney-Ni and NaHCO₃

In this example, 15.52 grams of a sample of WR Grace Raney-nickel 2800 was added to the autoclave (Reactor 100) as slurry in 500 ml of water. The autoclave level control was set up to maintain 500 ml of liquid holdup volume in the reactor. A continuous flow of hydrogen was provided and the reactor pressure was controlled in the range of 1000 psig. The catalyst was washed with deionized water at a rate of 5 ml per minute until the pH of the reactor effluent reached near neutrality. The catalyst was then activated by ramping up the temperature to 100° C. and holding at temperature for one hour. Reactor 200 was kept offline in this example.

Two separate feed solutions were prepared using deionized water as solvent, one solution containing 10.0% wt concentration of glucose and the other containing 1.0% wt concentration of NaHCO₃ as the pH control agent. The initial reaction conditions were: reaction temperature of 50° C., pressure of 1000 psig, hydrogen flow rate of 25 standard liters per hour, and stirrer RPM of 1250. The glucose feed was pumped into the reactor at a flow rate of 300 grams per hour. The rate of flow of NaHCO₃ solution was varied from 0 to 90 grams per hour. The reaction temperature was raised in steps to higher temperatures.

Samples of product stream 13 were analyzed by pH probe and HPLC to determine pH and the concentrations of the various products. The experimental results are given in Table 3.

TABLE 3

| Run Time [Hour] | Sample | Rxn Temp [° C.] | *Conc to Rxn Mixture | | Conc in Product Total Glycols, % Wt | pH | % Wt Yields | | | | | Total Glycols | Wt Ratio EG/PG |
|---|---|---|---|---|---|---|---|---|---|---|---|---|---|
| | | | Glucose | NaHCO3 | | | Glucose | Sorbitol | EG | PG | 12BDO | | |
| 7.0 | 3A | 100 | 10.00 | 0.00 | 0.00 | 4.3 | 9.2 | 91.5 | 0.0 | 0.0 | NA | 0.0 | |
| 9.6 | 3B | 150 | 10.00 | 0.00 | 0.00 | 4.1 | 0.8 | 100.9 | 0.0 | 0.0 | NA | 0.0 | |
| 17.2 | 3C | 165 | 9.52 | 0.05 | 0.00 | 4.3 | 0.5 | 97.5 | 0.0 | 0.0 | NA | 0.0 | |
| 25.2 | 3D | 175 | 9.09 | 0.09 | 0.14 | 6.6 | 1.3 | 94.0 | 1.4 | 0.1 | NA | 1.5 | 17.0 |
| 32.6 | 3E | 185 | 9.09 | 0.09 | 0.15 | 5.8 | 0.9 | 87.2 | 1.3 | 0.3 | NA | 1.6 | 4.0 |

As shown in Table 3 above, a comparative example process demonstrates the criticality of the various features of the presently disclosed subject matter, and without the combination of these various features, the desired results are not achieved. In this comparative example, a carbohydrate feed was contacted with a heterogeneous hydrogenation catalyst but without a retro-Aldol catalyst. The carbohydrate feed included a concentration of carbohydrate (i.e., glucose) of on average 10 wt %. The pH of the reaction was controlled to be in the range of from 2-7. The temperature of the reaction was between 100-185° C., which is lower than the desired range according to the presently disclosed process of 180-250° C., and 210-250° C. Without the combination of all the various features of the presently disclosed subject matter, desirable product yields are not achieved. As shown, the concentration of glycols in the product stream is not at least 5 wt %, and instead was 0.14-0.15 wt %. The total glycols yield was 1.5-1.6 wt %, with some samples showing 0 wt %. Another desired result is a yield of less than 10 wt % sorbitol; however, as shown, a sorbitol yield of greater than 85 wt % was achieved. Another feature of the presently disclosed subject matter is the ability to maximize the production of EG relative to PG. However, as shown, the without the combination of the disclosed process parameters, the comparative example process only achieved a yield of 1.3-1.4 wt % EG. Further, the comparative example process provided 4:1 and 17:1 EG/PG wt % yield ratios.

As shown in the Examples section above, the presently disclosed method for producing ethylene glycol from a carbohydrate feed has numerous advantages over the prior art. The disclosed method provides for various process conditions that, when combined, achieve superior results in terms of product yield, catalyst stability, and extended run time (e.g., suitable for commercialization). The presently disclosed method allows for the use of a carbohydrate feed with a high carbohydrate concentration and by running the reaction under pH controlled conditions, superior results and advantages over the prior art are achieved. As a result, the presently disclosed method has the advantages of achieving high total glycol yield (i.e., EG, PG, 1,2BDO), high EG:PG ratio, high EG:1,2BDO ratio, and having a stable catalyst system for at least 24 hours, at least 50 hours, and at least 100 hours.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

That which is claimed is:

1. A method for producing ethylene glycol from a carbohydrate feed comprising:
    a) contacting, in a first reactor under hydrogenation conditions, the carbohydrate feed with a bi-functional catalyst system comprising:
        1) a heterogeneous hydrogenation catalyst, and
        2) a soluble retro-Aldol catalyst;
        and, wherein the carbohydrate feed comprises a concentration of carbohydrate, in the total solution entering the first reactor, of 5-40 wt % in a solvent;
    b) running the reaction under pH controlled conditions for at least 24 hours and wherein the pH of the reaction is in the range of from 2-7, wherein the pH is controlled using at least one pH controlling agent selected from the group consisting of: alkali- and alkaline-earth metal salts of carbonic acid or carboxylic acids or combinations thereof, alkali- and alkaline-earth metal salts of phosphoric acid, zinc carbonate, and zinc salts of carboxylic acids;
    c) obtaining an intermediate product stream, from the first reactor, comprising ethylene glycol; and wherein the hydrogenation conditions comprise a temperature in the range of from 180-250° C.

2. The method of claim 1, wherein the carbohydrate feed comprises a concentration of carbohydrate, in the total solution entering the first reactor, of 10-40 wt % in a solvent.

3. The method of claim 2, wherein the solvent is $H_2O$.

4. The method of claim 1, wherein the first reactor is pre-loaded with the heterogeneous hydrogenation catalyst and the soluble retro-Aldol catalyst is continuously added to the first reactor.

5. The method of claim 4, wherein the soluble retro-Aldol catalyst is continuously added to the first reactor via the carbohydrate feed.

6. The method of claim 1, wherein the carbohydrate feed comprises one or more selected from the group consisting of: glucose, sucrose, xylose, sugar cane molasses, starch, and cellulose.

7. The method of claim 1, wherein the heterogeneous hydrogenation catalyst is a Raney-type catalyst.

8. The method of claim 7, wherein the heterogeneous hydrogenation catalyst comprises at least one selected from the group consisting of: Raney-Ni, Raney-Co, Raney-Cu, Raney-Ru, Cu, Co, Ru, and nano-particle metal.

9. The method of claim 8, wherein the heterogeneous hydrogenation catalyst is further promoted with one or more promoters selected from the group consisting of: Fe, Cr, Mn, Mo, W, Re, Rh, Pd, Ag, Au, Pt, Ir, and La.

10. The method of claim 1, wherein the soluble retro-Aldol catalyst comprises at least one selected from the group consisting of: silver tungstate, sodium meta-tungstate, ammonium meta-tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silico-tungstic acid, alkali- and alkaline-earth metal niobates.

11. The method of claim 1, wherein the temperature is in the range of from 210-250° C.

12. The method of claim 1, wherein the intermediate product stream comprises at least 5 wt % concentration of glycols.

13. The method of claim 1, wherein the intermediate product stream comprises a yield of no more than 10 wt % sorbitol.

14. The method of claim 1, wherein the intermediate product stream comprises a yield of at least 60 wt % EG.

15. The method of claim 1, wherein the intermediate product stream comprises an EG/PG wt % yield ratio of at least 7:1.

16. The method of claim 1, wherein the intermediate product stream comprises a yield of less than 3 wt % 1,2-butanediol.

17. The method of claim 1, further comprising running the reaction for a time period of at least 100 hours.

18. The method of claim 1, further comprising feeding the intermediate product stream to a second reactor comprising:
    (a) contacting the intermediate product stream from the first reactor with hydrogen in the presence of a heterogeneous hydrogenation catalyst; and
    (b) obtaining a final product stream comprising ethylene glycol.

* * * * *